(12) United States Patent  
Pipenhagen

(10) Patent No.: US 9,795,476 B2
(45) Date of Patent: Oct. 24, 2017

(54) COLLAPSIBLE HEART VALVE WITH ANGLED FRAME

(75) Inventor: Catherine A. Pipenhagen, Chanhassen, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 4 days.

(21) Appl. No.: 13/703,978

(22) PCT Filed: Jun. 14, 2011

(86) PCT No.: PCT/US2011/001070
§ 371 (c)(1),
(2), (4) Date: Feb. 27, 2013

(87) PCT Pub. No.: WO2011/159342
PCT Pub. Date: Dec. 22, 2011

(65) Prior Publication Data
US 2013/0166023 A1    Jun. 27, 2013

Related U.S. Application Data

(60) Provisional application No. 61/355,639, filed on Jun. 17, 2010.

(51) Int. Cl.
*A61F 2/06* (2013.01)
*A61F 2/24* (2006.01)

(52) U.S. Cl.
CPC .......... *A61F 2/2403* (2013.01); *A61F 2/2418* (2013.01); *A61F 2220/0066* (2013.01); *A61F 2230/008* (2013.01); *A61F 2230/0054* (2013.01); *A61F 2250/0037* (2013.01)

(58) Field of Classification Search
CPC .. A61F 2/2418; A61F 2/82; A61F 2/91; A61F 2/2412; A61F 2002/075; A61F 2002/821; A61F 2/07; A61F 2/86; A61F 2002/823
USPC ................................................. 623/1.11–1.54
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report & Written Opinion dated Sep. 23, 2011 for Application No. PCT/US2011/001070.

(Continued)

*Primary Examiner* — Ann Schillinger
(74) *Attorney, Agent, or Firm* — Lerner, David, Littenberg, Krumholz & Mentlik, LLP

(57) ABSTRACT

A prosthetic heart valve includes a stent and a valve assembly attached to the stent. The stent has a longitudinal axis, a distal end and a proximal end adapted to reside adjacent the aortic annulus of a patient. The proximal end of the stent is oriented at an oblique angle to the longitudinal axis.

13 Claims, 3 Drawing Sheets

(56) References Cited

U.S. PATENT DOCUMENTS

| | | |
|---|---|---|
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,800,520 A * | 9/1998 | Fogarty ............... A61F 2/07 606/194 |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,299,637 B1 * | 10/2001 | Shaolian ............ A61F 2/2418 623/1.24 |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 * | 4/2006 | Gabbay .................. 623/2.13 |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| 7,972,378 B2 * | 7/2011 | Tabor et al. ............... 623/2.17 |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2003/0167089 A1 | 9/2003 | Lane |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0021816 A1 * | 1/2007 | Rudin ............................ 623/1.4 |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0183273 A1 | 7/2008 | Mesana et al. |
| 2008/0183279 A1 * | 7/2008 | Bailey et al. .............. 623/1.24 |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 2047824 A1 | 4/2009 |

(56) References Cited

FOREIGN PATENT DOCUMENTS

| | | |
|---|---|---|
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2009045338 A1 | 4/2009 |
| WO | 2009132187 A1 | 10/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Ruiz, Carlos, Overview of PRE-CE Mark Transcatheter Aortic Valve Technologies, Euro PCR, dated May 25, 2010.
Percutaneous aortic valve replacement: resection before implantation, 836-840, Quaden, Rene et al., European J. of Cardio-thoracic Surgery, 27 (2005).
Catheter-implanted prosthetic heart valves, Knudsen, L.L., et al., The International Journal of Artificial Organs, vol. 16, No. 5 1993, pp. 253-262.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
U.S. Appl. No. 29/375,243, filed Sep. 20, 2010.
U.S. Appl. No. 29/375,260, filed Sep. 20, 2010.

* cited by examiner

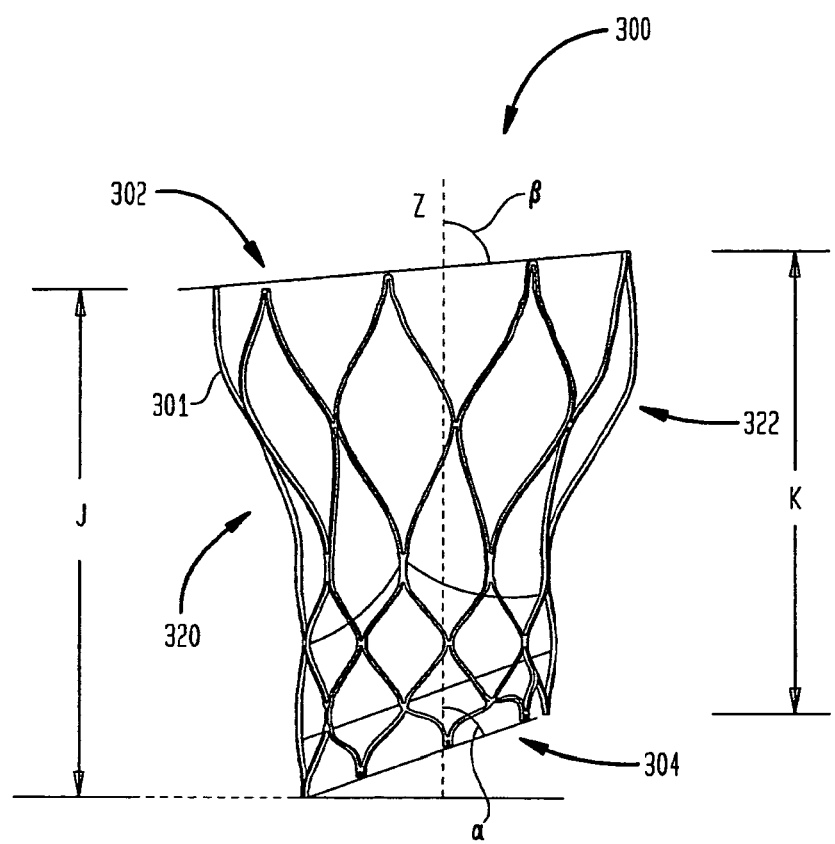

COLLAPSIBLE HEART VALVE WITH ANGLED FRAME

CROSS-REFERENCE TO RELATED APPLICATIONS

The present application is a national phase entry under 35 U.S.C. §171 of International Application No. PCT/US2011/001070, filed Jun. 14, 2011, published in English, which claims priority from U.S. Provisional Application No. 61/355,639, filed Jun. 17, 2010, all of which are incorporated herein by reference.

BACKGROUND OF THE INVENTION

The present disclosure relates to prosthetic heart valves and, more specifically, to prosthetic heart valves having an angled stent frame.

A healthy aortic valve acts as a one-way valve, opening to allow blood to flow out of the left ventricle of the heart, and then closing to prevent blood from flowing back into the heart. Diseased or damaged aortic valves may not close properly and thus allow blood to flow back into the heart. Damage to aortic valves may occur due to congenital defects, the natural aging process, infection or scarring. Diseased or damaged aortic valves sometimes need to be replaced to prevent heart failure. In such cases, collapsible prosthetic heart valves may be used to replace the native aortic valve.

Current collapsible prosthetic heart valve designs may be used in high-risk patients who may need a cardiac valve replacement, but who are not appropriate candidates for conventional open-chest, open-heart surgery. These collapsible and re-expandable prosthetic heart valves can be implanted transapically or percutaneously through the arterial system. One percutaneous delivery method entails introducing a collapsible prosthetic heart valve through a patient's femoral artery. This delivery method is referred to as a transfemoral approach.

With reference to FIGS. 1 and 2, a conventional collapsible prosthetic heart valve 1 typically includes a stent 10 for securing the prosthetic heart valve 1 to the patient's native valve annulus and a valve assembly 20 for controlling blood flow. Valve assembly 20 includes a plurality of leaflets 26 attached inside of stent 10. Stent 10 has a distal end 2, a proximal end 4, a first side 22 and a second side 24. The first side 22 and second side 24 of stent 100 have the same, or a substantially similar, height $H_4$. As seen in FIG. 2, due to the anatomy and acute curvature of the aortic arch A, conventional stent 10 and valve assembly 20 cannot always be aligned with the native valve annulus N. When conventional prosthetic heart valve 1 is deployed near the native aortic valve, stent 10 and valve assembly 20 may be canted toward the descending aorta at the valve annulus N. As a consequence, prosthetic valve leaflets 26 will not be in alignment with the native valve leaflets. The improper positioning of the leaflets 26 with respect to the valve annulus N may adversely affect the functioning of conventional prosthetic heart valve 1. In addition, the orientation of conventional prosthetic heart valve 1 at an oblique angle relative to aortic valve annulus N may exert uneven forces on surrounding tissue, including the mitral valve annulus, or otherwise interfere with the proper function of the mitral valve. In light of the issues described above, improvements to current prosthetic heart valve designs are desirable.

SUMMARY OF THE INVENTION

The present disclosure relates to prosthetic heart valves and the use of the same to treat patients. In one embodiment, the prosthetic heart valve includes a stent and a valve assembly attached to the stent. The stent has a proximal end adapted to reside adjacent the aortic annulus, a distal end, a first side having a first length between the proximal end and the distal end, and a second side having a second length between the proximal end and the distal end. The second length is less than the first length.

In another embodiment, the prosthetic heart valve includes a stent and a valve assembly attached to the stent. The stent has a longitudinal axis, a distal end, and a proximal end adapted to reside adjacent the aortic annulus. The proximal end of the stent is oriented at a first oblique angle to the longitudinal axis. The first oblique angle may be between about 5° and about 25°. Preferably, the first oblique angle is about 15°. The valve assembly may be attached to the stent at a second oblique angle to the longitudinal axis. The second oblique angle may be substantially equal to the first oblique angle.

The prosthetic heart valve has a first side having a first length between the proximal end and the distal end and a second side having a second length between the proximal end and the distal end. The second length may be less than the first length.

In some embodiments, the distal end of the stent may be oriented substantially orthogonally to the longitudinal axis. Alternatively, the distal end of the stent may be oriented at a second oblique angle to the longitudinal axis. The second oblique angle may be between about 5° and about 25°, and preferably is about 15°. The second oblique angle may be about equal to the first oblique angle. In these embodiments, the valve assembly may be attached to the stent at a third oblique angle to the longitudinal axis. The first oblique angle, the second oblique angle and the third oblique angle may be substantially equal.

The present disclosure further relates to methods of replacing a native heart valve of a patient, the native heart valve having a valve annulus and valve leaflets. The method may include providing a prosthetic heart valve including a stent and a valve assembly attached to the stent, the stent having a longitudinal axis, a distal end, and a proximal end oriented at an oblique angle to the longitudinal axis; and implanting the prosthetic heart valve in the patient so that the proximal end of the stent is substantially parallel with the valve annulus. The implanting step may include deploying the prosthetic heart valve using a transapical procedure, a transfemoral procedure or a transseptal procedure. The implanting step may further include implanting the prosthetic heart valve so that the valve assembly is substantially parallel with the valve annulus.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

FIG. 5 is a side view of a collapsible prosthetic heart valve according to an alternate embodiment of the present disclosure.

DETAILED DESCRIPTION

As used herein, the term "proximal," when used in connection with a prosthetic heart valve, refers to the end of the prosthetic heart valve closest to the heart when the heart valve is implanted in a patient, whereas the term "distal," when used in connection with a prosthetic heart valve, refers to the end of the heart valve farthest from the heart when the prosthetic valve is implanted in a patient. The term "proximal," when used herein in connection with a delivery device for a prosthetic heart valve, refers to the end of the delivery device closest to the operator, and the term "distal," when used herein in connection with a prosthetic heart valve delivery device, refers to the end of the delivery device farthest from the operator.

In all the embodiments disclosed herein, the stents are part of a collapsible prosthetic heart valve. The prosthetic heart valve has an expanded condition in which the stent is held in place in the aortic annulus primarily by outward radial forces.

Figure 3:
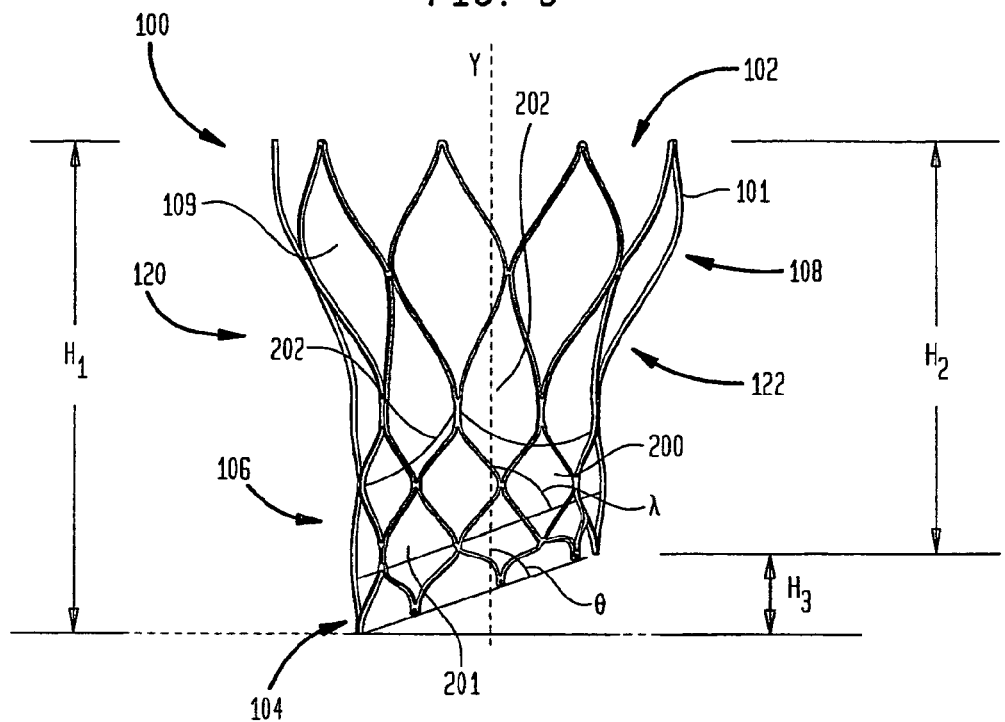
FIG. 3 is a side view of a collapsible prosthetic heart valve according to an embodiment of the present disclosure.
Figure 4:
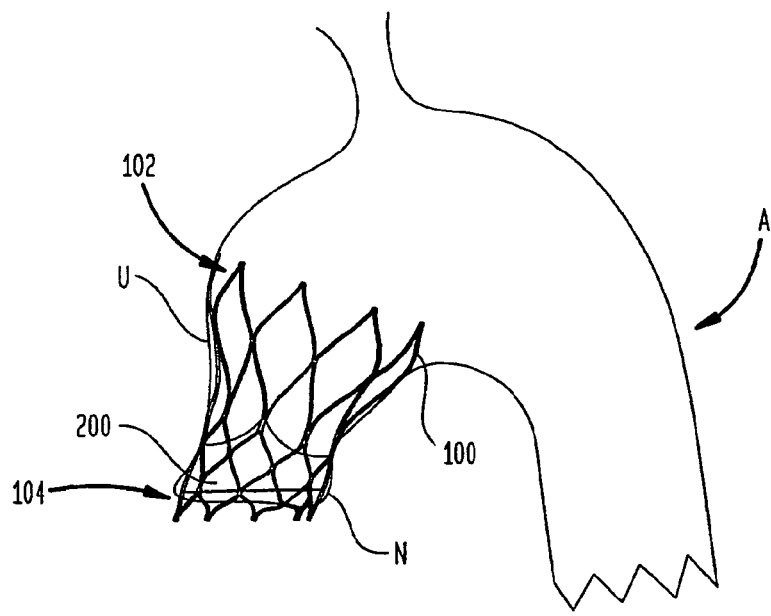
FIG. 4 is a highly schematic side view of the prosthetic heart valve of FIG. 3 positioned near a native aortic valve.

FIGS. 3 and 4 depict a collapsible prosthetic heart valve 100 designed to replace the function of a native aortic valve of a patient. Prosthetic heart valve 100 includes a stent or frame 101 which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides.

Prosthetic heart valve 100 also includes a valve assembly 200 supported by stent 101. Valve assembly 200 may include a cuff 201 and a plurality of leaflets 202 which collectively function as a one-way valve. Valve assembly 200 may be wholly or partly formed of tissue or any suitable polymer. U.S. Patent Application Publication Nos. 2008/0228264, filed Mar. 12, 2007 and 2008/0147179, filed Dec. 19, 2007, the entire disclosures of which are hereby incorporated by reference, describe suitable valve assemblies. Briefly, as described in these publications, each of leaflets 202 has one edge attached to stent 101 and a free edge. When the blood pressure on an inflow side of prosthetic heart valve 100 exceeds the blood pressure on the outflow side of the valve, the free edges of leaflets 202 can move away from one another to allow blood to flow through the valve. When the blood pressure on the inflow side of prosthetic heart valve 100 is no longer greater than the blood pressure on the outflow side of the valve, the free edges of leaflets 202 coapt to prevent blood from flowing in an opposite direction through the valve.

Stent 101 is formed with a plurality of cells 109 which define an annulus section 106 and an aorta section 108. In the expanded condition of stent 101, aorta section 108 may have a larger perimeter or circumference than annulus section 106. Cells 109 may have a substantially diamond shape when stent 101 is in the expanded condition, and may be arranged in one or more annular rows extending around the perimeter of stent 101. The cellular structure of stent 101 allows stent 101 to move from a collapsed condition for maneuvering to the proper position in the patient to an expanded condition for engagement in the annulus N of the patient's aortic valve. Stent 101 may include various other structures, such as features for attaching the commissure points of valve assembly 200, commissure posts, elongated struts for joining the cells of annulus section 106 to the cells of aorta section 108, and the like (none of which are shown).

The valve assembly 200 may be attached to the stent 101 at an oblique angle λ to the longitudinal axis Y of between about 5° and about 25°. Angle λ may be substantially similar to the angle θ formed by the proximal end 104 of the stent 101 with longitudinal axis Y. An angle λ of about 15° is highly preferred.

Stent 101 may additionally include any suitable marker (not shown) to aid the operator in aligning or orienting prosthetic heart valve 100 properly in the aortic annulus. The marker may help the operator position prosthetic heart valve 100 in the aortic annulus so that the second side 122 of stent 101 is situated closer to the mitral valve than the first side 120. The marker may constitute a band or other region of radiopaque material positioned on one or more commissure posts or on any other portions of stent 101. In some embodiments, the marker may be situated on second, side 122 of stent 101. Alternatively or additionally, a marker may be positioned in the delivery system to assist the operator in properly aligning the delivery system, and thus the prosthetic heart valve 100, in the aortic annulus.

The aorta section 108 of stent 101 terminates in a stent distal end 102 which is oriented substantially orthogonal to the longitudinal axis Y of stent 101. The annulus section 106 of stent 101, on the other hand, terminates in a stent proximal end 104 which is oriented at an oblique angle to the stent longitudinal axis Y. Preferably, the proximal end 104 of the stent 101 forms an angle θ with longitudinal axis Y of between about 5° and about 25°. An angle θ of about 15° is highly preferred.

Figure 1:
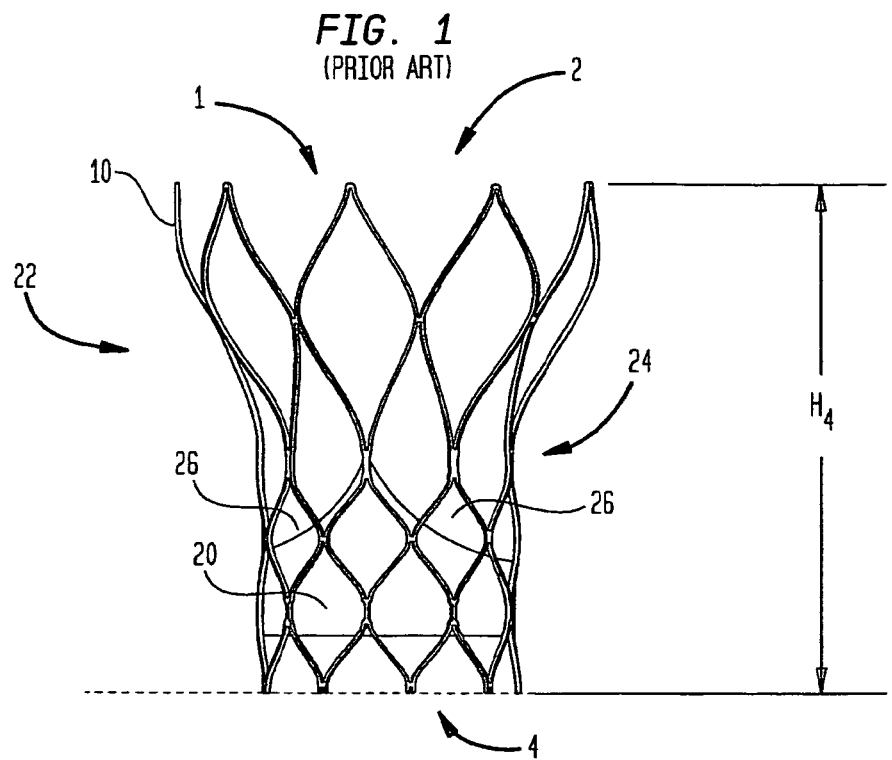
FIG. 1 is a side view of a conventional collapsible prosthetic heart valve including a stent and valve leaflets supported therein.
Figure 2:
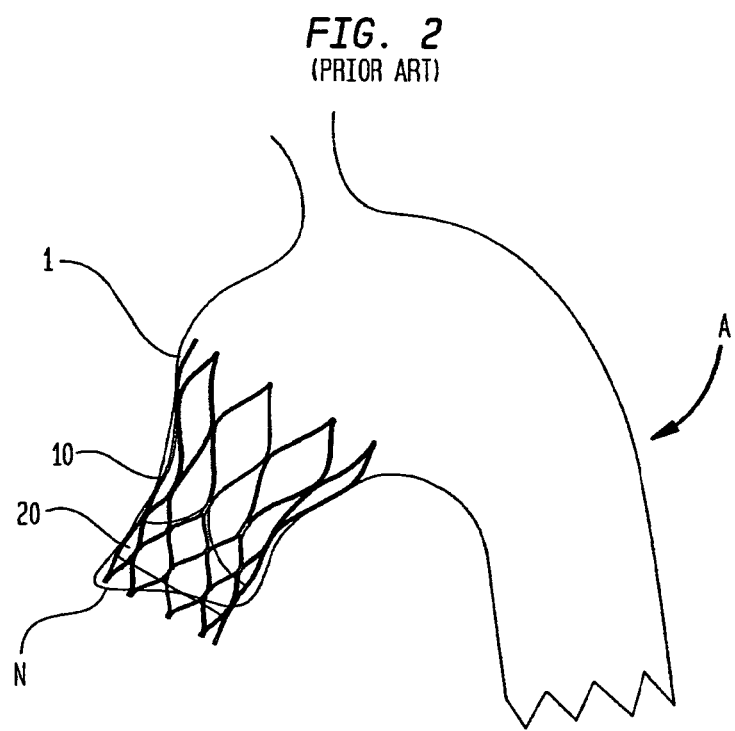
FIG. 2 is a highly schematic side view of the collapsible prosthetic heart valve of FIG. 1 positioned near a native aortic valve.

A length or height $H_1$ in the direction of longitudinal axis Y is defined between distal end 102 and proximal end 104 on the first side 120 of stent 101. Similarly, a length or height $H_2$ in the longitudinal direction is defined between distal end 102 and proximal end 104 on the second side 122 of stent 101. As seen in FIG. 3, because the proximal end 104 of stent 101 is at an oblique angle to the longitudinal axis Y while the distal end 102 is orthogonal to the longitudinal axis Y, height $H_1$ is longer than height $H_2$. In some embodiments, height $H_1$ may be substantially similar to the height $H_4$ of conventional stent 10 (see FIG. 1). Preferably, height $H_2$ is shorter than the height $H_4$ of conventional stent 10 to prevent or reduce the possibility of prosthetic heart valve 100 interfering with the proper functioning of the mitral valve, as discussed in the background section above. FIG. 3 also shows a distance or height $H_3$, which represents the difference between height $H_1$ and height $H_2$. Height $H_3$ is less than heights $H_1$ and $H_2$.

Using minimally invasive surgical procedures, the prosthetic heart valve 100 may be implanted in the valve annulus N of the patient's native aortic valve. In particular, the annulus section 106 of stent 101 is positioned in aortic valve annulus N, whereas the aorta section 108 of stent 101 is positioned in the aorta A, typically downstream (in the direction of blood flow) from the patient's valsalva sinus.

An operator may implant prosthetic heart valve 100 in a patient using any suitable delivery system. Various delivery systems can be utilized to deliver and deploy the prosthetic heart valve 100 at the intended target site. The delivery system may depend to some extent on the desired valve implantation approach; for example, whether transapical, transseptal or transfemoral techniques are used. Although the delivery systems may include certain variations depending on the delivery approach, all such delivery systems may have similar valve interface mechanisms for retaining the valve in a collapsed condition during delivery to a target site and subsequently deploying it in a controlled manner.

The prosthetic heart valve 100 is assembled to the delivery system in a collapsed condition. The delivery system maintains the prosthetic heart valve 100 in the collapsed condition until the operator actuates a deployment mechanism of the delivery system. Typically, the delivery system includes a sheath which surrounds the prosthetic heart valve 100 and maintains it in the collapsed condition.

To deploy the prosthetic heart valve 100, the operator may slide the sheath of the delivery system in either a proximal (toward the operator) or distal (away from the operator) direction to uncover the prosthetic heart valve 100. As the sheath is removed, the uncovered portions of prosthetic heart valve 100 will begin to expand radially.

With reference to FIG. 4, prosthetic heart valve 100 is deployed in the aortic annulus so that the aorta section 108 of stent 101 engages a portion U of the ascending aorta A, while the annulus section 106 of the stent engages the aortic annulus N. Preferably, the orientation of stent 101 is such the second side 122 of the stent is positioned closer to the mitral valve than the first side 120. This may be accomplished by observing the radiopaque markers (not shown) on stent 101 and rotating the delivery catheter until the stent is in the proper rotational orientation.

With stent 101 properly implanted in a patient, the proximal end 104 of stent 101 will preferably be substantially parallel to and slightly upstream of the aortic annulus N, with leaflets 202 appropriately positioned relative to the aortic annulus. Due to the angled feature of stent 101, the leaflets 202 can be more accurately positioned relative to the patient's aortic annulus N, thereby improving the overall functioning of the prosthetic heart valve 100. As discussed above, the valve assembly 200 may be attached to the stent 101 at an oblique angle λ to the longitudinal axis Y. As such, the prosthetic heart valve 100 may be implanted adjacent the valve annulus N of a patient so that the valve assembly 200 is substantially parallel with the valve annulus.

The angled proximal end 104 of stent 101 of prosthetic heart valve 100 makes it easier for the operator to align the prosthetic heart valve with the native aortic leaflets or aortic annulus. The improved positioning capability of prosthetic heart valve 100 minimizes the need for repositioning the prosthetic heart valve once it has been deployed. As discussed above, an operator can cover or uncover the prosthetic heart valve 100 with the sheath of the delivery system to expand or collapse the prosthetic heart valve. When using a conventional prosthetic heart valve 10, the operator might need to collapse the prosthetic heart valve after deployment to reposition it in the aortic annulus. In the case of prosthetic heart valve 100, however, the operator may not need to reposition the prosthetic heart valve because of its improved positioning capability. Thus, the operator may not need to cover stent 101 again with the sheath of the delivery system. As a consequence, it may be possible to form the sheath of the delivery system of more flexible materials.

FIG. 5 shows an alternate embodiment of a prosthetic heart valve 300. Prosthetic heart valve 300 is substantially similar to prosthetic heart valve 100 described above. However, rather than having a stent distal end that is oriented substantially orthogonally to the longitudinal axis Z of stent 301, the distal end 302 of stent 301 is oriented at an oblique angle β to the longitudinal axis. Angle β may be the same as the angle α between the proximal end 304 of stent 301 and longitudinal axis Z. Alternatively, angle β may be greater than or less than angle α. Preferably, both angle α and angle β are between about 5° and about 25°, with angles of about 15° being highly preferred.

Stent 301 has a length or height J in the direction of longitudinal axis Z between distal end 302 and proximal end 304 on a first side 320 of the stent. Similarly, a second side 322 of stent 301 has a length or height K in the direction of longitudinal axis Z between distal end 302 and proximal end 304. Height J may be greater than or less than height K depending on the relative sizes of angles α and β. Where angles α and β are about the same, heights J and K will be substantially equal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a stent extending in a length direction between a proximal end and a distal end, the stent having a collapsed condition and an expanded condition, a longitudinal axis, and an annulus section adapted to reside adjacent the aortic annulus in a patient, the annulus section having a circumference and including a plurality of cells each having a cell end not connected to other cells, the cell ends collectively defining the proximal end of the stent and including a first cell end spaced farther in the length direction from the distal end of the stent than each of the other cell ends, and a second cell end spaced closer in the length direction to the distal end of the stent than each of the other cell ends, the second cell end being positioned opposite the first cell end around the circumference of the annulus section such that an imaginary line connecting the first cell end to the second cell end defines a slope oriented at a first oblique angle to the longitudinal axis of the stent; and
a valve assembly attached to the stent, the valve assembly including a cuff, a plurality of leaflets, and a longitudinal axis, the cuff having a circumference and a proximal edge, the proximal edge defining a straight line from one side of the circumference of the cuff to an opposite side of the circumference of the cuff when viewed in a direction orthogonal to the longitudinal axis of the stent, the valve assembly being attached to the stent so that the longitudinal axis of the valve assembly is at a second oblique angle to the longitudinal axis of the stent and so that the proximal edge of the cuff is at another oblique angle to the longitudinal axis of the stent, each of the leaflets having a free edge, the leaflets having an open condition in which the free edges are spaced apart from one another to define a flow passageway through the stent, and a closed condition in which the free edges of the leaflets coapt to close the flow passageway through the stent.

2. The prosthetic heart valve of claim 1, wherein the stent has a first side having a first length between the proximal end and the distal end, and a second side opposite the first side and having a second length between the proximal end and the distal end, the second length being less than the first length.

3. The prosthetic heart valve of claim 1, wherein the second oblique angle is between about 5° and about 25°.

4. The prosthetic heart valve of claim 3, wherein the second oblique angle is about 15°.

5. The prosthetic heart valve of claim 1, wherein the first oblique angle is substantially equal to the second oblique angle.

6. The prosthetic heart valve of claim 1, wherein the distal end of the stent is oriented substantially orthogonally to the longitudinal axis of the stent.

7. The prosthetic heart valve of claim 1, wherein the first oblique angle is between about 5° and about 25°.

8. The prosthetic heart valve of claim 7, wherein the first oblique angle is about 15°.

9. The prosthetic heart valve of claim 1, wherein the distal end of the stent is oriented at a third oblique angle to the longitudinal axis of the stent.

10. The prosthetic heart valve of claim 9, wherein the third oblique angle is between about 5° and about 25°.

11. The prosthetic heart valve of claim 10, wherein the third oblique angle is about 15°.

12. The prosthetic heart valve of claim 9, wherein the third oblique angle is about equal to the first oblique angle.

13. The prosthetic heart valve of claim 9, wherein the first oblique angle, the second oblique angle and the third oblique angle are substantially equal.

* * * * *